United States Patent
Kajii et al.

(10) Patent No.: US 8,632,844 B2
(45) Date of Patent: Jan. 21, 2014

(54) METHOD FOR THE MANUFACTURE OF NERVE REGENERATION-INDUCING TUBE

(75) Inventors: Fumihiko Kajii, Ohtsu (JP); Hidenori Tanaka, Ohtsu (JP); Yuta Kawakatsu, Ohtsu (JP); Susumu Kashiwabara, Ohtsu (JP); Masaki Sato, Osaka (JP)

(73) Assignee: Toyo Boseki Kabushiki Kaisha, Osaka (JP)

( * ) Notice: Subject to any disclaimer, the term of this patent is extended or adjusted under 35 U.S.C. 154(b) by 446 days.

(21) Appl. No.: 12/744,179

(22) PCT Filed: Dec. 4, 2008

(86) PCT No.: PCT/JP2008/072038
§ 371 (c)(1),
(2), (4) Date: May 21, 2010

(87) PCT Pub. No.: WO2009/072552
PCT Pub. Date: Jun. 11, 2009

(65) Prior Publication Data
US 2010/0249811 A1   Sep. 30, 2010

(30) Foreign Application Priority Data
Dec. 7, 2007  (JP) .................................. 2007-317462

(51) Int. Cl.
*A61K 9/00*   (2006.01)
*A61L 33/00*   (2006.01)
*B05D 3/00*   (2006.01)
*B01J 13/22*   (2006.01)

(52) U.S. Cl.
USPC .......................... 427/2.24; 427/2.21; 427/2.25

(58) Field of Classification Search
USPC .......................................... 427/2.27; 606/152
See application file for complete search history.

(56) References Cited

U.S. PATENT DOCUMENTS 5,986,168 A * 11/1999 Noishiki ........................ 424/422
6,335,007 B1 * 1/2002 Shimizu et al. ............. 424/78.08

(Continued)

FOREIGN PATENT DOCUMENTS

JP   5-237139 A    9/1993
JP   2000-60956 A  2/2000

(Continued)

OTHER PUBLICATIONS

International Search Report of PCT/JP2008/072038, maling date of Jan. 20, 2009.

(Continued)

*Primary Examiner* — Dah-Wei Yuan
*Assistant Examiner* — Diane Zhang
(74) *Attorney, Agent, or Firm* — Westerman, Hattori, Daniels & Adrian LLP

(57) ABSTRACT

A method for manufacturing a nerve regeneration-inducing tube with excellent pressure resistance, shape recovery property, anti-kink property, film exfoliation resistance, resistance to invasion of outer tissues, and leakage resistance. The tubular body is formed by weaving together fibers made up of biodegradable polymer. The outer surface of the tubular body is coated multiple times with a collagen solution. The lumen of the tubular body is filled with collagen. Viscosity of the collagen solution that is first applied to the outer surface of the tubular body is between 2 to 800 cps. Viscosity of the collagen solution that is subsequently applied is higher than viscosity of the first applied collagen solution.

11 Claims, 3 Drawing Sheets

(56) References Cited

U.S. PATENT DOCUMENTS

| | | | |
|---|---|---|---|
| 6,589,257 B1 * | 7/2003 | Shimizu | 606/152 |
| 7,084,082 B1 | 8/2006 | Shimizu | |
| 8,367,148 B2 * | 2/2013 | Greenhalgh et al. | 427/2.24 |
| 2005/0085901 A1 * | 4/2005 | Castro et al. | 623/1.39 |
| 2006/0177475 A1 * | 8/2006 | Rueger et al. | 424/422 |
| 2006/0216320 A1 | 9/2006 | Kitazono et al. | |
| 2009/0297692 A1 * | 12/2009 | Castro et al. | 427/2.25 |

FOREIGN PATENT DOCUMENTS

| | | |
|---|---|---|
| JP | 2000-325463 A | 11/2000 |
| JP | 2001-70436 A | 3/2001 |
| JP | 2002-320630 A | 11/2002 |
| JP | 2003-19196 A | 1/2003 |
| WO | 98/22155 A1 | 5/1998 |
| WO | 99/63908 A1 | 12/1999 |
| WO | 2004/087012 A1 | 10/2004 |

OTHER PUBLICATIONS

European Search Report dated Dec. 20, 2012, issued in corresponding European patent application No. 08856086.7.

Nakamura, Tasuo, et al., "Experimental study on the regeneration of peripheral nerve gaps through a polyglycolic acid-collagen (PGA-collagen) tube", Brain Research, vol. 1027, No. 1-2, p. 18-29, Nov. 19, 2004; cited in European Search Report dated Dec. 20, 2012.

* cited by examiner compressing until the strain rate becomes 50% being allowed to stand for 10 minutes after detaching the weight measuring height of tube measuring length L when the kink is generated kink generation

METHOD FOR THE MANUFACTURE OF NERVE REGENERATION-INDUCING TUBE

TECHNICAL FIELD OF THE INVENTION

The present invention relates to a method for the manufacture of a nerve regeneration-inducing tube by which peripheral nerve cut or excised by accident or surgical operation is reconnected utilizing the elongation of nerve cells. More particularly, the present relates to a method where close adhesion of a tubular body comprising a biodegradable polymer constituting the nerve regeneration-inducing tube with collagen applied on the outer surface of the tubular body is enhanced whereby the initial strength, flexibility, etc. of the entire nerve regeneration-inducing tube are improved.

BACKGROUND ART

There are many examples where damage of peripheral nerve caused by accident or the like is unable to be completely restored. There are also many clinical examples where peripheral nerve must be excised as a result of surgical operations in general. In the damage of peripheral nerves, autologous nerve grafting has been an only means besides a direct anastomosis. However, the result thereof is not always satisfactory but recovery of sensory perception and capacity for locomotion are bad and the aftereffect due to erroneous governing is noted as well. In addition, there are many patients complaining not only the aftereffect such as pain and deficiency in sensory perception but also the abnormal sensory perception of the diseased area or, particularly, pain.

An attempt for the regeneration of nerve by connection of gaps of peripheral nerve using a connecting tube made of artificial materials has been briskly carried out since early 1980's. However, all of the studies of connecting channels using non-absorptive synthetic artificial materials have resulted in failure. In order to solve the above, it is necessary to consider in the followings such as that invasion of connective tissues from outside is prevented during the regeneration of nerve bundles, that substance interchange inside and outside the channels or neogenesis of capillary blood vessels in channel walls is necessary, that a substance acting as a scaffold suitable for the growth of Schwann cells and axon in the channel is necessary and that, after the regeneration, the used material is degraded and absorbed. Taking those conditions into consideration, studies for artificial nerve connecting tube by a biodegradable and absorbable material have been carried out thereafter.

With regard to the regeneration of peripheral nerve, attempts for extending the distance between the stumps which are able to be regenerated using a silicone tube have been conducted since a silicone tube model was reported in 1982. However, since nutrients are unable to permeate through the wall of silicone tube, there is a problem such as that the nutrients are not sufficiently provided to nerve axon whereby capillary blood vessel is unable to be produced in silicone and no satisfactory nerve regeneration has been available even when a silicone tube is used. Further, even if the nerve is able to be regenerated, there is a problem that the silicone tube which is a foreign substance anyway must be removed by means of further surgical operation, etc.

On the other hand, regeneration of peripheral nerve using a tube comprising a biodegradable polymer in place of a silicone tube has been attempted. When a nerve regeneration tube comprising a biodegradable polymer is used, the nerve regeneration tube is gradually degraded and absorbed in vivo by hydrolysis or by the action of enzymes after the nerve is regenerated whereby there is no need of taking out it by a means such as further surgical operation.

With regard to a nerve regeneration tube comprising a biodegradable polymer as such, there is a disclosure in, for example the Patent Document 1, for an auxiliary material for nerve regeneration which comprises bundles of collagen fiber on which laminin and fibronectin are coated. In the Patent Document 2, there is a disclosure for an artificial nerve tube which comprises a tubular body comprising biodegradable and absorbable material and, in the lumen of the tubular body, a collagen body having gaps and penetrating the tubular body nearly in parallel to the axial line of said tubular body where the gap is filled with a matrix gel containing collagen, laminin, etc. In the Patent Document 3, there is a disclosure for an artificial nerve tube which comprises a tubular body comprising biodegradable and absorbable material and laminin-coated collagen fiber bundles inserted into the lumen of the tubular body nearly in parallel to the axial line of the tubular body. In the Patent Document 4, there is a disclosure for a substrate material for the reconstruction of nerves having a structure where fibers comprising a bioabsorbable material are bundled. In the Patent Document 5, there is a disclosure for a support such as sponge, tube or coil comprising collagen. In the Patent Document 6, there is a disclosure for a support which is composed of a spongy fine matrix comprising a biodegradable material or a bioabsorbable material and a linear biotissue induction path or a linear organ induction path. In the Patent Document 7, there is a disclosure for a nerve regeneration tube containing a sponge comprising a biodegradable polymer material and a reinforcing material comprising a biodegradable polymer having longer period for degradation and absorption than that of said sponge wherein the inner side thereof comprises sponge.

The nerve regeneration tubes as such are usually manufactured in such a manner that collagen is applied to the outer surface of the tubular body knitted with ultrafine fiber comprising the biodegradable polymer and then collagen is filled in the inner area of the tubular body. However, since the close adhesion of the collagen applied to the outer surface of the tubular body with the biodegradable polymer of the tubular body is poor, there is a problem in the strength, the flexibility, etc. in its actual use.

(Patent Documents)

1. Japanese Patent Application Laid-Open (JP-A) No. 237139/93
2. WO 98/22155
3. WO 99/63908
4. Japanese Patent Application Laid-Open (JP-A) No. 2000-325463
5. Japanese Patent Application Laid-Open (JP-A) No. 2001-70436
6. Japanese Patent Application Laid-Open (JP-A) No. 2002-320630
7. Japanese Patent Application Laid-Open (JP-A) No. 2003-19196

BRIEF DESCRIPTIONS OF DRAWINGS

DISCLOSURE OF THE INVENTION

Figure 1:
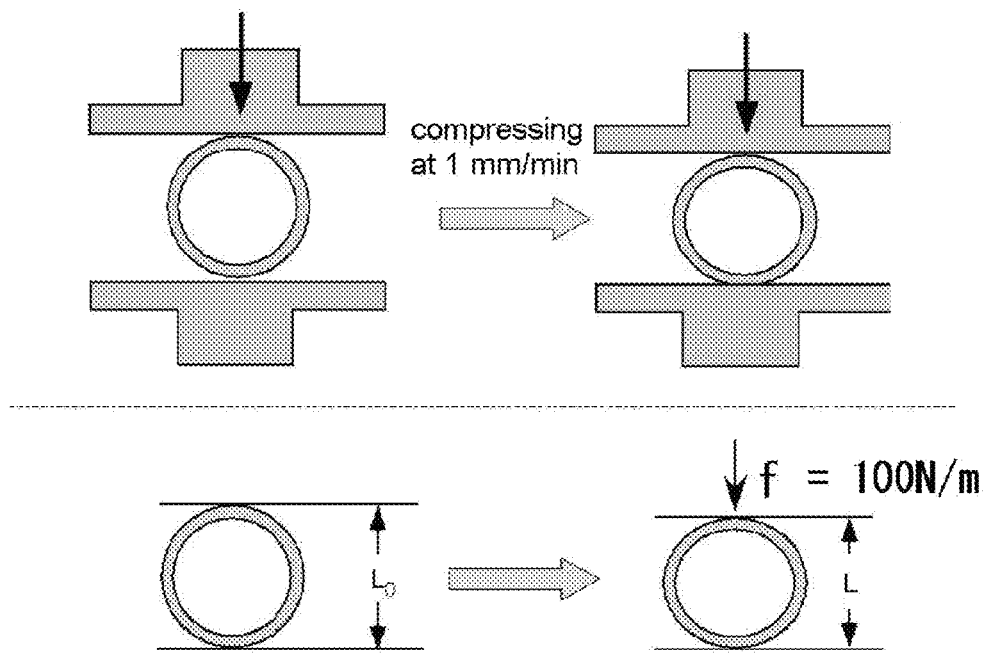
FIG. 1 is an illustrative drawing for the method of evaluation of pressure resistance.

Problem that the Invention is to Solve

The present invention has been created in view of the current status of the prior art as such and an object of the present invention is to provide a method for the manufacture of a nerve regeneration-inducing tube where a collagen solution is applied on the outer surface of a tubular body knitted with ultrafine fiber comprising a biodegradable polymer while collagen is filled in the inner area of the tubular body, which nerve regeneration-inducing tube is excellent in pressure resistance, shape recovery property, anti-kink property, film exfoliation resistance, property of prevention of invasion of outer tissues and leakage resistance.

Means for Solving the Problem

In order to achieve the object as such, the present inventor has conducted extensive investigation for a method where close adhesion of the tubular body knitted from the biodegradable polymer fiber with collagen applied onto the outer surface thereof is enhanced and, as a result, it has been found that a nerve regeneration-inducing tube excellent in pressure resistance, shape recovery property, anti-kink property, film exfoliation resistance, property of prevention of invasion of outer tissues and leakage resistance is able to be manufactured in high efficiency when viscosity (or concentration) of the collagen solution firstly applied to the outer surface of the tubular body is made low and, in the application thereafter, viscosity (or concentration) of the collagen solution is made higher than before whereupon the present invention has been achieved.

Thus, the present invention is a method for the manufacture of a nerve regeneration-inducing tube in which the outer surface of the tubular body knitted with a plurality of ultrafine fibers comprising biodegradable polymer is coated by application of a collagen solution for plural times and then collagen is filled in the inner area of the above tubular body, characterized in that, viscosity of the collagen solution which is firstly applied on the outer surface of the tubular body is made 2 cps to 800 cps or, preferably, 5 cps to 200 cps.

In the preferred embodiment of the method of the present invention, viscosity of a collagen solution to be applied later is made high as compared with that of the firstly-applied one where the viscosity is preferably made high in two or more stages. Alternatively, a collagen solution in the viscosity of the collagen solution which is firstly applied to the outside of the tubular body is applied for plural times.

Furthermore, in the preferred embodiment of the method of the present invention, the biodegradable polymer is at least one polymer which is selected from the group consisting of polyglycolic acid, polylactic acid and a lactic acid-caprolactone copolymer. The present invention also relates to a nerve regeneration-inducing tube which is characterized in being manufactured by the above method.

Advantages of the Invention

In the manufacturing method of the present invention, viscosity (or concentration) of the collagen solution which is firstly applied to the outer surface of the tubular body knitted with a biodegradable polymer fiber is made low whereby it is now possible to provide a nerve regeneration-inducing tube in which the tubular body comprising the biodegradable polymer is uniformly and tightly adhered to collagen and which is excellent in pressure resistance, shape recovery property, anti-kink property, film exfoliation resistance, property of prevention of invasion of outer tissues and leakage resistance.

BEST MODE FOR CARRYING OUT THE INVENTION

In the method of the present invention, the nerve regeneration-inducing tube is manufactured in such a manner that a collagen solution is applied for plural times to outer surface of a tubular body knitted with plural ultrafine fibers comprising a biodegradable polymer to coat and collagen is further filled in the lumen of the tubular body.

Examples of the biodegradable polymer constituting the tubular body include polylactic acid, polyglycolic acid, polycaprolactone, a lactic acid-glycolic acid copolymer, a lactic acid-caprolactone copolymer, a glycolic acid-caprolactone copolymer, polydioxanone and glycolic acid-trimethylenecarboxylic acid. In view of easy availability and handling, it is preferred to use polyglycolic acid, polylactic acid or a lactic acid-caprolactone copolymer and it is particularly preferred to use polyglycolic acid. Each of those biodegradable polymers may be used solely or two or more thereof may be used by mixing.

In the present invention, diameter of the ultrafine fiber comprising the biodegradable polymer is preferred to be from 1 to 50 μm. When the fiber diameter is too small, the fiber gap becomes dense whereby it may happen that collagen is hardly permeated into the tubular body or that flexibility of the tubular body lowers. On the contrary, when the fiber diameter is too large, the retained amount of collagen becomes small whereby it may happen that the growing speed of the nerve does not rise or that the strength of the tubular body becomes insufficient. More preferably, diameter of the ultrafine fiber is 3 to 40 μm, and further preferably 6 to 30 μm.

In the formation of the tubular body, it is preferred that 5 to 60 of the ultrafine fibers comprising the biodegradable polymer and having the above fiber diameter are bundled and alternately knitted as warps and woofs. When the numbers of the ultrafine fibers to be bundled are too small, it may happen that the strength of the tubular body becomes insufficient or that a sufficient retained-amount of collagen is unable to be secured. On the contrary, when the numbers of the ultrafine fibers to be bundled are too many, it may happen that a tubular body in fine diameter is unable to be prepared or that flexibility of the tubular body are unable to be secured. More preferably, the numbers of the ultrafine fibers are 10 to 50, and further preferably 20 to 40.

When a tubular body is formed by an alternate knitting of the ultrafine fiber bundles, the pore size of the network is preferred to be about 5 to 300 μm, and more preferably 10 to 200 μm. When the pore size of the network is too small, it may happen that growth of the cells and the tissues is inhibited due to the lowering of invasion of capillary blood vessel or due to the lowering of water permeability. When it is more than about 300 μm, invasion of the tissues becomes excessive whereby growth of the cells and the tissues may be inhibited.

It is preferred that although inner diameter and outer diameter of the tubular body are decided to accord with the size of the nerve to be connected and, when the production cost and the time limitation are taken into consideration, it is preferred that many kinds of tubular bodies where the sizes are varied are previously prepared. Although the size of the tubular body depends on the site of the nerve to be regenerated and on the necessary strength, it is usual that the inner diameter is 0.1 to 20 mm, the outer diameter is 0.15 to 25 mm, the wall thickness is 0.05 to 5 mm and the length is 1.0 to 150 mm. When the wall thickness is too thick, that may obstruct the regeneration of the biotissues while, when it is too thin, degradation and absorption of the tubular body are too quick whereby the shape may not be held until the regeneration of the nerve finishes. Further, when the inner diameter to the nerve to be connected is too big, there is a possibility that elongation of the nerve is unable to be done appropriately.

In the present invention, the outer surface of the tubular body is coated by applying a collagen solution for several times by a method which has been known among persons skilled in the art while the inner area (lumen) of the tubular body is filled by charging collagen therein. With regard to the collagen to be used for application to the outer surface of the tubular body and for filling into the inside of the tubular body, there may be used collagen which has been conventionally used as a scaffold for nerve regeneration. Examples thereof include type I collagen, type III collagen, and type IV collagen and the like and each of them may be used solely or plural ones may be used by mixing. With regard to the collagen, it is preferred to use a purified one where concentration of sodium chloride contained therein is made 2.0% by weight or less, preferably 0.1 to 1.5% by weight on a dry basis. The collagen may also contain laminin, heparan sulfate proteoglycan, entactin and growth factor. Examples of the growth factor include EGF (epidermal growth factor), βFGF (fibroblast growth factor), NGF (nerve growth factor), PDGF (platelet-derived growth factor), IGF-1 (insulin-like growth factor) and TGF-β (transforming growth factor). With regard to the collagen solution, it is preferred that, after every one application thereof in a form of a solution in hydrochloric acid using a brush or a writing brush, the solution is completely dried and then the next application is conducted whereby a plurality of applications are done.

The most important feature of the method of the present invention is that, when the outer surface of the tubular body is applied with a collagen solution, a low-viscosity solution of 2 to 800 cps, preferably 5 to 200 cps is used as a collagen solution for the first application. Frequency of the application of this low-viscosity solution is preferred to be from once to ten times, preferably once to five times. As a result of application of the low-viscosity solution of said range firstly, the collagen solution is well permeated among the ultrafine fibers of the biodegradable polymer constituting the tubular body whereby adhesion and unified feel of the biodegradable polymer with collagen is able to be significantly enhanced. When a high-viscosity solution having higher viscosity than the above is applied firstly, the collagen solution is unable to be permeated among the ultrafine fibers whereby the collagen becomes a filmy state after drying whereupon there is a risk that collagen is exfoliated from the tubular body. When such a nerve regeneration-inducing tube is used, there is resulted inhibition of invasion of the blood vessel into the tubular body or inhibition of growth of nerve cells.

In the method of the present invention, it is preferred that, firstly, a low-viscosity collagen solution is applied for several times so as to form a sealing of gap between fibers constituting the tubular body and a thin layer and then a collagen solution of higher viscosity of 200 to 30,000 cps is applied thereon. That is because, in an application of the low-viscosity solution only, very many times of application are necessary for achieving a predetermined thin layer thickness whereby the working ability is bad. Frequency of the application of this high-viscosity solution is desired to be from once to fifty times, preferably once to thirty times. When the frequency of application of the high-viscosity solution is too many, that causes a lowering of the shape recovery property and, for example, when a diseased area is crushed with something after the surgical operation, the strain resulted on the tube is not recovered whereby it may clog the nerve regeneration path. Further, since collagen has a relatively quick biodegradation speed, there is little merit even when the application frequency is increased too much.

Actually, it is preferred that the viscosity of the collagen solution is made higher in multiple stages of two or more after the first application of the low-viscosity solution. For example, the viscosity of the collagen solution to be applied can be raised in three stages of 2 to 200 cps, 200 to 3,000 cps and 3,000 to 30,000 cps. In that case, permeation among the ultrafine fibers of the tubular body and formation of film on the surface are conducted by the first low-viscosity solution, adhesion to this film is done using the next medium-viscosity solution to conduct the sealing of the network and the last high-viscosity solution is adhered to this sealed collagen layer to enhance the strength whereby the coating with a strong initial strength is able to be efficiently carried out. Further, the gap of the viscosity applied in a stepwise manner as such is made little whereby it is possible to improve the operating ability of the applying work or to reduce the uneven application or the place left unapplied.

It is preferred that the tubular body where collagen is coated or filled is subjected to freezing, freeze-drying and cross-linking treatments to cross-link the collagen. Preferably, the freezing is carried out under the condition of −10 to −196° C. for 3 to 48 hours. As a result of the freezing, fine ice is formed among the collagen molecules and the collagen solution results in a phase separation to give sponge. After that, the above frozen collagen solution is freeze-dried in vacuo preferably at about −40 to −80° C. and preferably about 12 to 48 hours. As a result of freeze-drying, fine ice among the collagen molecules is evaporated and, at the same time, the collagen sponge becomes fine. Examples of the cross-linking method include γ-ray cross-linking, ultraviolet cross-linking, electronic ray cross-linking, thermal dehydration cross-linking, glutaraldehyde cross-linking, epoxy cross-linking and water-soluble carbodiimide cross-linking and, among them, a thermal dehydration cross-linking where the cross-linking degree is able to be easily controlled and living body is not effected even by conducting the cross-linking treatment is preferred. The thermal dehydration cross-linking is conducted in vacuo at, for example, about 105 to 150° C., more preferably about 120 to 150° C., and further preferably about 140° C. for about 6 to 24 hours, more preferably about 6 to 12 hours, and further preferably about 12 hours. When the cross-linking temperature is too high, there is a possibility that the strength of the biodegradable and absorbable material lowers while, when it is too low, there is a possibility that no sufficient cross-linking reaction takes place.

Since the tubular body comprising the biodegradable polymer and the collagen are tightly adhered with each other in the nerve regeneration-inducing tube manufactured as mentioned above, the initial strength and elasticity which are not lower than the sum of the strength of each are available. To be more specific, in the nerve regeneration-inducing tube of the present invention, the strain rate (pressure resistance) when compression is done by applying the load of 100 N/m from the side in the direction of diameter is not more than 15%, preferably 0.1 to 10% and, further, the recovery rate (shape recovery property) in 50% of the strain when similar compression is done so as to generate of 50% strain of the tube (until the diameter of the tube becomes one half) is not less than 60%. Pressure resistance is on the assumption of the resistance to the load for the nerve regeneration-inducing tube due to the work by a medical device upon connection of nerve and to the treatment after the surgical operation and, generally, the more the thickness of the collagen layer, the more the pressure resistance. However, when the tubular body and collagen are not tightly adhered with each other but the film is separated, the pressure resistance is not able to be so much expected. In addition, the shape recovery property is on an assumption for a recovery of the shape from the strain due to the work by a medical device upon connection of nerve (such as too strong picking by a pair of tweezers) or the shock to the diseased area after the surgical operation and, if the shape recovery property is low, strain remains in the tube and the nerve growth path is inhibited.

Further, the nerve regeneration-inducing tube of the present invention has a limiting curved rate (anti-kink property) of not less than 10% and also has a high resistance to exfoliation of the film. The limiting curved rate shows the range where bending is possible without causing a kink and is an index concerning the movable region upon connection of the nerve. When the limiting curve rate is less than 10%, it is not possible to use for the case where a curved nerve growth path is necessary and, even if used, tension is applied to the nerve and there is a risk of causing the inhibition of growth of the nerve and the inflammation caused by compression of outer tissues. Resistance to exfoliation of the film is the resistance to exfoliation and crack of the coated collagen. The reason why collagen is coated on the entire outer surface of the tubular body is to prevent the invasion of outer tissue to the nerve growth path (invasion of outer tissues-prevention property) and to prevent the leakage of the collagen sponge in the inner area of the tubular body to outside (leakage resistance) and, when the coated collagen is exfoliated or cracked, there is a risk that the above properties are unable to be secured. In the nerve regeneration-inducing tube of the present invention, the tubular body and collagen are tightly adhered with each other and there is no separated film whereby a high anti-kink property is able to be achieved and, at the same time, there is no possibility that the exfoliation and the crack as such are resulted.

In the nerve regeneration-inducing tube of the present invention, a big effect is also able to be expected for the adjustment of the degrading rate for bioabsorbency. When a nerve regeneration-inducing tube constituted from a biodegradable tubular body and collagen sponge and coated collagen is embedded in a body, strength of the coated collagen is lost since collagen is firstly degraded. However, when the method of the present invention is used, strength of the tubular body is able to be maintained for a long period since the degrading rate of collagen adhered to the gap between the tubular body fibers is retarded. Further, since the gap between the tubular body fibers is able to be sealed for a long period of time whereby it is possible to prevent the invasion of outer tissues which have a risk of inhibiting the growth of nerve cells. The reason why the degrading rate becomes slow is likely to be due to the fact that the collagen adhered to the gaps of the tubular body fibers has small contact area to the body fluid and to the outer tissues.

EXAMPLES

The effect of the nerve regeneration-inducing tube manufactured by the method of the present invention will be shown below although the present invention is not limited thereto. Incidentally, the evaluation of the nerve regeneration-inducing tube obtained in the Examples was done in accordance with the following methods.

Evaluation Method (1) Pressure Resistance

A load was applied at 100 N/m in a diameter direction from the side of a sample in the length of 5 mm as shown in FIG. 1 under the following measuring condition. Then, diameter height (L) in the load direction was measured whereupon a strain rate=$(L/L_0) \times 100$ (wherein, $L_0$ is a diameter height in the load direction before applying the load) was calculated. Incidentally, the sample was measured for the case of without aging and also for the case of with aging using a physiological saline solution for one, two, three and four week(s).

Measuring Condition

Temperature: 200° C.; humidity: 65.0%

Tester: Tensilon (UTA-1t).

Testing speed: 1 mm/min

Load cell rating: 5 kgf

Sample numbers: N=3

(2) Shape Recovery Property

Figure 2:
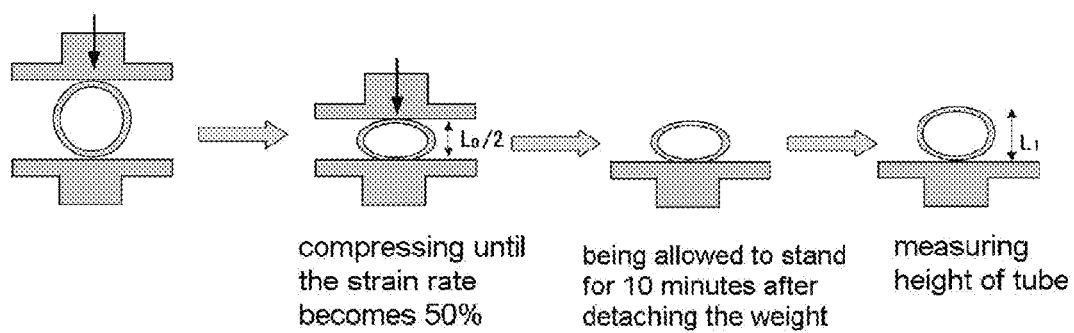
FIG. 2 is an illustrative drawing for the method of evaluation of shape recovery property.

A sample was compressed until the strain rate became 50% in the diameter direction from the side of the sample in a length of 5 mm as shown in FIG. 2 under the same measuring condition as in the above (1) pressure resistance. Immediately after the compression, the weight was detached and the sample was allowed to stand for 10 minutes. Then, diameter height ($L_1$) in the load direction was measured whereupon a shape recovery rate=$[(L_1-2/L_0)/(2/L_0)] \times 100$ (wherein, $L_0$ is a diameter height in the load direction before applying the load) was calculated.

(3) Anti-Kink Property

Figure 3:
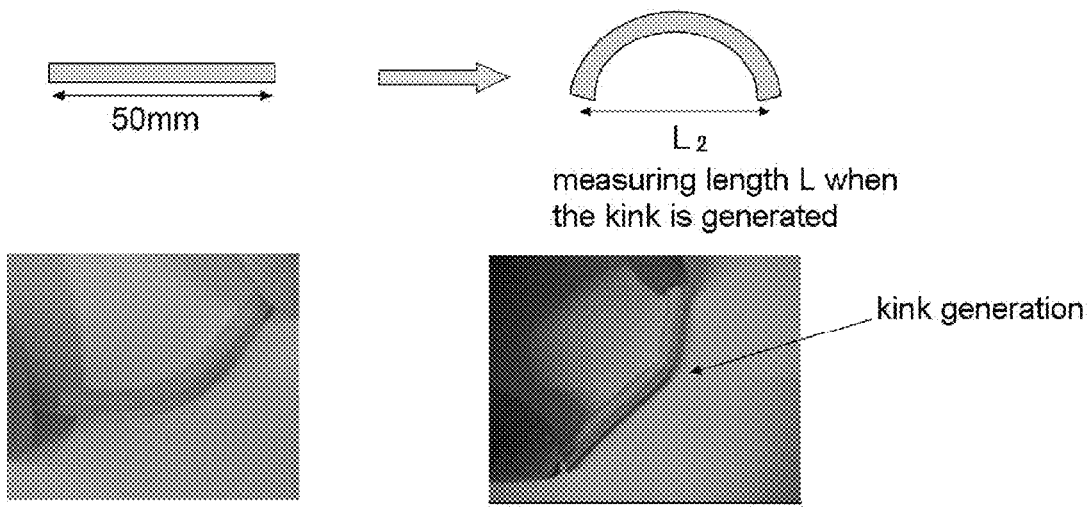
FIG. 3 is an illustrative drawing for the method of evaluation of anti-kink property.

As shown in FIG. 3, at the temperature of 20.0° C. and the humidity of 65.0%, a sample in the length of 50 mm was bent by hand at the rate of about 1 mm/second and the length ($L_2$ mm) when the kink was generated in the sample was measured whereupon a limiting curved rate $[1-(L_2/50)] \times 100$ was calculated. Incidentally, the numbers of the measured sample were made N=3.

(4) Film Exfoliation Resistance

Figure 4:
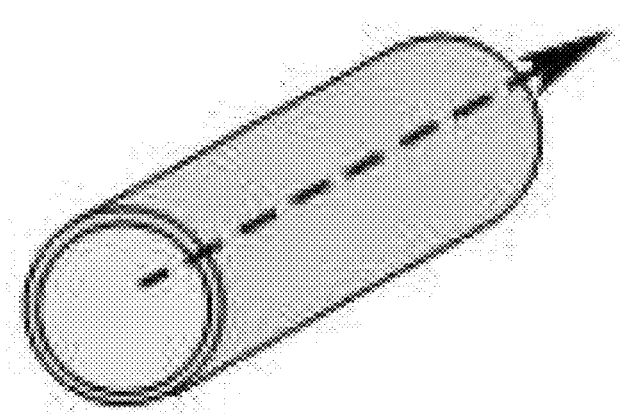
FIG. 4 is an illustrative drawing for the method of evaluation of film exfoliation resistance.
Figure 5:
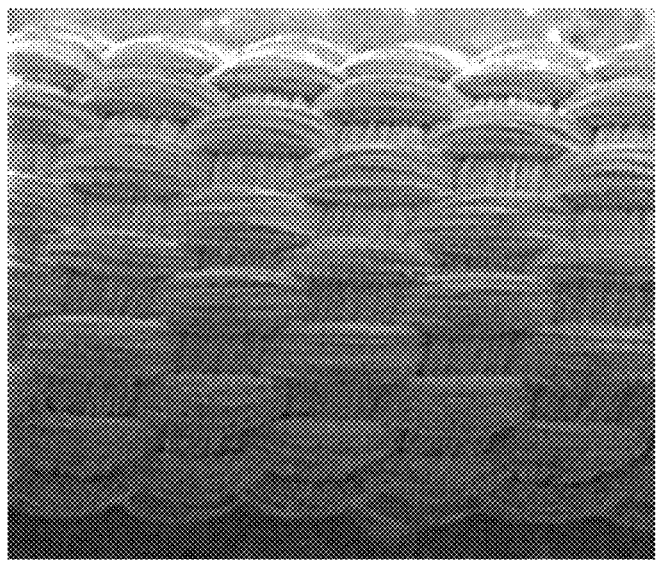
FIG. 5 shows an SEM image (50×) of the tubular body of Example.

As shown in FIG. 4, at the temperature of 20.0° C. and the humidity of 65.0%, a side of a sample in the length of 5 mm was cut with scissors and it was confirmed whether the collagen film on the outer surface of the sample was able to be exfoliated and separated. Further, the picture of the outer surface of the sample was taken under an SEM and it was confirmed whether partial exfoliation or crack of the film was noted. Incidentally, numbers of the sample to be measured were made N=3.

(5) Cell Invasion Preventing Property and Leakage Resistance

At the temperature of 25.0° C. and the humidity of 60.0%, a 1.0% by weight collagen solution prepared by the method which will be mentioned later was filled in the inner area of the sample in the length of 5 mm. After that, it was confirmed every ten minutes by naked eye whether the filled collagen leaked out from the side of the sample and the time until the leakage was confirmed was recorded. When the time until the collagen solution is completely frozen is taken into consideration, it is necessary that the leakage resistance is not shorter than 2 hours or, at least, not shorter than 1 hour.

Preparation of Collagen Solutions

Into a plastic bottle was placed 392 g of a 0.001 mol/l hydrochloric acid (pH 3), then 8 g of NMP collagen PS (manufactured by Nippon Meat Packers, Inc.) was placed and the mixture was well stirred to dissolve whereupon a collagen solution in which the final concentration of collagen was 2.0% by weight was prepared. This collagen solution was diluted with the above hydrochloric acid to prepare collagen solutions in which the final concentration of collagen was 0.1, 0.2, 0.5, 0.7 and 1.0% by weight each.

Measurement of Viscosity of Collagen Solutions

Each of the collagen solutions where collagen concentration was 0.1, 0.2, 0.5, 0.7, 1.0 and 2.0% by weight each was stabilized at the temperature of 10° C. using a constant-temperature vessel in which cooling water of 10° C. were circulated, then a B type viscometer (product name: Visco Basic plus, manufactured by FUNGILAB, rotor used: L3 spindle, measuring rotation number: 20 rpm, test number: N=3) was made to act, the measured values after 3, 4 and 5 minutes from the acting were read and the mean value thereof was adopted as a measured viscosity. The result is shown in Table 1.

TABLE 1

| | collagen concentration (% by weight) | | | | | |
|---|---|---|---|---|---|---|
| | 0.1 | 0.2 | 0.5 | 0.7 | 1.0 | 2.0 |
| viscosity (CPS) | 17 | 40 | 925 | 2580 | 7542 | 25367 |

Fiber bundle where 28 ultrafine fibers (diameter: about 15 μm) comprising polyglycolic acid were bundled was used as warp and woof and alternately knitted to prepare a cylindrical tubular body of 3 mm inner diameter and 50 mm length.

brush made of Teflon (registered trade mark) and air-dried and, after confirming that it was completely dried, next application was successively conducted. Concentration and applying times of the collagen solution to be applied were in accordance with the description mentioned in the application method in Table 2 and the applications were successively carried out from the solution where the collagen concentration was lower. After completion of applications of the collagen solutions, a 1.0% by weight collagen solution was filled into the lumen of the tubular body and frozen at −40° C. The frozen one was freeze-dried and, after that, a thermal cross-linking was carried out in vacuo (not higher than 1 Pa) at 140° C. for 24 hours in order to cross-link the collagen molecule and the resulting one was used as a sample for each of Examples 1 to 8 and Comparative Example 1. The sample of Comparative Example 2 was the same as others except that application of the collagen solution was not carried out.

Evaluation Result

Pressure resistance, shape recovery property, anti-kink property, film exfoliation resistance, cell invasion preventing property and leakage resistance were evaluated for the samples of the above Examples 1 to 8 and Comparative Examples 1 and 2. The results are shown in Table 2.

TABLE 2

| | | sample No. | | | | | | | | | |
|---|---|---|---|---|---|---|---|---|---|---|---|
| | | Example 1 | Example 2 | Example 3 | Example 4 | Example 5 | Example 6 | Example 7 | Example 8 | Comparative Example 1 | Comparative Example 2 |
| application method | 0.1 wt % | — | — | — | — | — | — | 5 times | 3 times | — | — |
| | 0.2 wt % | 2 times | 2 times | 2 times | 2 times | 2 times | 2 times | — | — | 0 time | 0 time |
| | 0.5 wt % | 1 time | 1 time | 1 time | 1 time | 1 time | 1 time | — | 1 time | 0 time | 0 time |
| | 0.7 wt % | — | — | — | — | — | — | 25 times | — | — | — |
| | 1.0 wt % | 17 times | 25 times | 20 times | 10 times | 5 times | 1 time | — | — | 20 times | 0 time |
| | 1.5 wt % | — | — | — | — | — | — | — | 10 times | — | — |
| strain at 100 N/m | without aging | 5.7% | 2.7% | 3.9% | 3.9% | 3.9% | 6.5% | 5.2% | 4.9% | 16.2% | 48.5% |
| | 1 week | 30.2% | 29.0% | 29.0% | 19.8% | 23.5% | 25.8% | 30.9% | 29.8% | 35.5% | 55.2% |
| | 2 weeks | 43.0% | 40.0% | 38.8% | 47.3% | 43.5% | 37.0% | 44.1% | 42.4% | 52.5% | 56.8% |
| | 3 weeks | 59.2% | 52.7% | 55.8% | 55.5% | 58.0% | 56.2% | 60.7% | 58.4% | 64.5% | 68.9% |
| | 4 weeks | 70.7% | 61.8% | 69.3% | 71.2% | 76.0% | 64.3% | 72.5% | 69.8% | 66.6% | 72.5% |
| shape recovery rate | | 75.7% | 68.5% | 70.1% | 79.1% | 82.8% | 85.1% | 75.6% | 74.7% | 42.6% | 81.3% |
| limiting curved rate | | 13.8% | 11.0% | 14.4% | 17.0% | 19.4% | 20.4% | 14.0% | 14.8% | 3.6% | 23.0% |
| film separation | | absent | absent | absent | absent | absent | absent | absent | absent | present | absent |
| exfoliation or crack observed by SEM | | absent | absent | absent | absent | absent | absent | absent | absent | present | absent |
| time until the filled liquid leaks | | 180 min | 220 min | 190 min | 130 min | 90 min | 60 min | 200 min | 190 min | 180 min | 10 min |
| judgment | pressure resistance | ○ | ○○ | ○○ | ○○ | ○○ | ○ | ○ | ○○ | ○ | Δ |
| | shape recovery property | ○ | ○ | ○ | ○ | ○○ | ○○ | ○ | ○ | Δ | ○○ |
| | anti-kink property | ○ | ○ | ○ | ○○ | ○○ | ○○ | ○ | ○ | Δ | ○○ |
| | film exfoliation resistance | ○ | ○ | ○ | ○ | ○ | ○ | ○ | ○ | Δ | ○ |
| | cell invasion preventing property and leakage resistance | ○○ | ○○ | ○○ | ○○ | ○ | ○ | ○○ | ○○ | ○○ | Δ |

Examples 1 to 8, and Comparative Examples 1 and 2

The above collagen solution was uniformly applied for one time onto the outer surface of the above tubular body using a It is apparent from the results of Table 2 that the nerve regeneration-inducing tubes manufactured by the method of the present invention are excellent in pressure resistance, shape recovery property, anti-kink property, film exfoliation resistance, cell invasion preventing property and leakage resistance as compared with the conventional ones.

INDUSTRIAL APPLICABILITY

Since the nerve regeneration-inducing tube manufactured by the method of the present invention is excellent in the above-mentioned properties, it is excellent in the maintenance of quality during storage or transport, in the handling during the clinical use and in the stability as well as safety after the surgical operation whereby it is quite useful in the medical treatment for nerve regeneration.

The invention claimed is:

1. A method for manufacturing a nerve regeneration-inducing tube, comprising the steps of:
    applying at least one coat of a first collagen solution to an outer surface of a tubular body, the tubular body being formed by weaving together a plurality of fibers;
    applying at least one coat of a second collagen solution to the outer surface of the tubular body, the outer surface having been coated with the first collagen solution; and
    filling an inner area of the tubular body with collagen,
    wherein each of the fibers comprises a biodegradable polymer,
    wherein viscosity of the first collagen solution is 5 cps to 200 cps, and
    wherein viscosity of the second collagen solution is higher than viscosity of the first collagen solution.

2. The method according to claim 1, wherein viscosity of the collagen solution is increased in two or more increments.

3. The method according to claim 1, wherein viscosity of the second collagen solution is 200 cps to 30,000 cps.

4. The method according to claim 1, wherein the biodegradable polymer is at least one polymer which is selected from the group consisting of polyglycolic acid, polylactic acid and a lactic acid-caprolactone copolymer.

5. The method according to claim 1, wherein the fibers have a diameter of 1 to 50 μm.

6. The method according to claim 5, wherein the fibers have a diameter of 3 to 40 μm.

7. The method according to claim 6, wherein the fibers have a diameter of 6 to 30 μm.

8. The method according to claim 3,
    wherein viscosity of the first collagen solution is 5 cps to 200 cps, and
    wherein viscosity of the second collagen solution is 200 cps to 3,000 cps.

9. The method according to claim 1, further comprising a third collagen solution,
    wherein viscosity of the third collagen solution is higher than viscosity of the second collagen solution.

10. The method according to claim 9, wherein viscosity of the third collagen solution is 200 cps to 30,000 cps.

11. The method according to claim 10, wherein viscosity of the third collagen solution is 3,000 cps to 30,000 cps.

* * * * *